United States Patent [19]
Davidson

[11] Patent Number: 5,152,794
[45] Date of Patent: Oct. 6, 1992

[54] ZIRCONIUM OXIDE AND NITRIDE COATED PROTHESIS FOR REDUCED MICROFRETTING

[75] Inventor: James A. Davidson, Germantown, Tenn.

[73] Assignee: Smith & Nephew Richards Inc., Memphis, Tenn.

[21] Appl. No.: 557,173

[22] Filed: Jul. 23, 1990

Related U.S. Application Data

[63] Continuation-in-part of Ser. No. 385,285, Jul. 25, 1989.

[51] Int. Cl.$^5$ .......................... A61F 2/28; A61F 2/30; A61F 5/04
[52] U.S. Cl. ...................................... 623/16; 623/18; 623/20; 623/22; 623/23; 606/60; 606/65; 606/69; 606/76
[58] Field of Search ........................ 623/16, 10, 20, 22

[56] References Cited

U.S. PATENT DOCUMENTS

| | | |
|---|---|---|
| 2,987,352 | 6/1961 | Watson . |
| 3,643,658 | 2/1972 | Steinemenan . |
| 3,677,795 | 7/1972 | Bokros et al. . |
| 4,040,129 | 8/1977 | Steinemann et al. . |
| 4,145,764 | 3/1979 | Suzuki et al. . |
| 4,159,358 | 6/1979 | Hench et al. . |
| 4,223,412 | 9/1980 | Aoyagi et al. . |
| 4,495,664 | 1/1985 | Blanquaert ........................... 623/18 |
| 4,608,051 | 8/1986 | Rick et al. ............................ 623/10 |
| 4,617,024 | 10/1986 | Broemer et al. ...................... 623/10 |
| 4,652,459 | 3/1987 | Engelhardt . |
| 4,652,534 | 3/1987 | Kasuga . |
| 4,671,824 | 6/1987 | Haygarth . |
| 4,687,487 | 8/1987 | Hintermann .......................... 623/18 |
| 4,714,474 | 12/1987 | Brooks, Jr. et al. .................. 623/20 |
| 4,728,488 | 3/1988 | Gillett et al. . |
| 4,834,756 | 5/1989 | Kenna .................................... 623/18 |
| 4,955,911 | 9/1990 | Frey et al. ............................. 623/16 |

FOREIGN PATENT DOCUMENTS

| | | |
|---|---|---|
| 770080 | 10/1967 | Canada . |
| 1140215 | 1/1983 | Canada . |
| 0038902 | 11/1981 | European Pat. Off. .............. 623/23 |
| 1325269 | 8/1973 | United Kingdom . |

OTHER PUBLICATIONS

Pamphlet, "Zircadyne Corrosion Properties", Teledyne Wah Chang Albany (no date).

Conte, Borello and Cabrini, "Anodic Oxidation of Zircaloy-2", Jnl. of Applied Electrochemistry, vol. 6, pp. 293-299 (1976).

Haygarth and Fenwick, "Improved Wear Resistance of Zirconium by Enhanced Oxide Films", Thin Solid Films, Metallurgical and Protective Coatings, vol. 118, pp. 351-362 (1984).

"The Cementless Fixation of Hip Endoprostheses", edited by Morscher, Mittelmeier, 'Total Hip Replacement with the Autophor Cement-Free Ceramic Prosthesis', pp. 225-241 (1984).

Brown and Merritt, "Evaluation of Corrosion Resistance of Bioly", Dept. of Biomedical Engineering, Case Western Reserve University, Feb. 13, 1986 (1:8).

(List continued on next page.)

*Primary Examiner*—David Isabella
*Attorney, Agent, or Firm*—Pravel, Gambrell, Hewitt, Kimball & Krieger

[57] ABSTRACT

Orthopedic implants of zirconium or zirconium-based alloy coated with blue or blue-black zirconium oxide or zirconium nitride to provide low friction, highly wear resistant coatings especially useful in artificial joints, such as hip joints, knee joints, elbows, etc. The invention zirconium oxide or nitride coated prostheses are also useful to reduce microfretting wear in multi-component surgical implants subject to such wear. Further, the coatings provide a barrier against implant corrosion caused by ionization of the metal prosthesis. Such protection can be extended by the use of oxidized or nitrided porous coatings of zirconium or zirconium alloy beads or wire mesh into which bone spicules may grow so that the prosthesis may be integrated into the living skeleton.

5 Claims, 3 Drawing Sheets

Davidson, Schwartz, Lynch, and Gir. "Wear, Creep and Frictional Heating of Femoral Implant Articulating Surfaces and the Effect on Long-Term Performance - Part II, Friction, Heating, and Torque", Jnl. of Biomedical Materials Research: Applied Biomaterials, vol. 22, No. A1, pp.6991 (1988).

ASTM F86-84, "Standard Practice for Surface Preparation and Marking of Metallic Surgical Implants", pp. 12-14 (1984), corrected editorially in May, 1987.

Khruschov, "Principles of Abrasive Wear" Wear, 28, 69-88 (1974).

Weightman and Light, "The Effect of the Surface Finish of Alumina and Stainless Steel on the Wear Rate of UHMW Polyethylene" Biomaterials, 7, 20-24 (1986).

Viegas, et al., "Metal Materials Biodegration: A Chronoamperometric Study", Journal of Materials Science:- Materials in Medicine 1, 105-109, (1990).

Briscoe, et al., "The Friction and Wear of High Density Polythene: The Action of Lead Oxide and Copper Oxide Fillers" Wear, 27, 19-34 (1974).

Rabinowicz, "Lubrication of Metal Surface by Oxide Films" ASLE Translations, 10, 400-407 (1967).

Mäusli, et al., "Constitution of Oxides on Titanium Alloys for Surgical Implants" Advances In Bio Materials, 8, 305 (1988).

Rokicki, "The Passive Oxide Film on Electropolished Titanium" (Feb. 1990).

Coll and Jacquot, "Surface Modification of Medical Implants and Surgical Devices Using TiN Layers" Surface and Coatings Technology 36, 867 (1988).

Bradhurst and Heuer, "The Influence of Oxide Stress on the Breakaway Oxidation of Zircaloy-2", J. of Nuclear Materials 37, 35 (1970).

Demizu, et al., "Dry Friction of Oxide Ceramics Against Metals: The Effect of Humdidty", Tribology Transactions 33, 505 (1990).

K. G. Budinski, "Tribological Properties of Titanium Alloys", pp. 289-299, vol. I, *Wear of Materials*, ASME (1991).

R. C. Bill, "Selected Fretting-Wear-Resistant Coatings for Ti-6%Al-% Alloy", Wear 106 (1985), pp. 283-301.

G. Bertrand et al., "Morphology of Oxide Scales Formed on Titanium", vol. 21, *Oxidation of Metals*, Nos. 1/2 (1983), pp. 1-19.

ZIRCONIUM OXIDE AND NITRIDE COATED PROTHESIS FOR REDUCED MICROFRETTING

This application is a continuation-in-part of U.S. Ser. No 385,285 filed Jul. 25, 1989.

BACKGROUND OF THE INVENTION

1. Field of Invention

This invention relates to metallic orthopedic implants with load bearing surfaces coated with a thin, dense, low friction, highly wear-resistant coating of zirconium oxide, nitride, carbide or carbonitride. This coating is especially useful on the portions of these prostheses which bear against surfaces which are subject to high rates of wear. An example is the femoral head of a hip-stem prosthesis which engages a counter-bearing surface in an acetabular cup which is often made of a softer material such as ultra-high molecular weight polyethylene.

The invention also relates to zirconium oxide and nitride coatings on the non-load bearing surfaces of an orthopedic implant where the zirconium oxide or nitride provides a barrier between the metallic prosthesis and body tissue thereby preventing the release of metal ions and corrosion of the implant. Additionally, in the preferred oxidation process by which zirconium oxide is produced, the associated increase in surface oxygen content and hardness increases the strength of the metal substrate and improves the fatigue properties of the implant.

2. Background

Orthopedic implant materials must combine high strength, corrosion resistance and tissue compatibility. The longevity of the implant is of prime importance especially if the recipient is relatively young because it is desirable that the implant should function for the complete lifetime of a patient. Because certain metal alloys have the required mechanical strength and biocompatibility, they are ideal candidates for the fabrication of prostheses. 316L stainless steel, chrome-cobalt-molybdenum alloys and more recently titanium alloys have proven to be the most suitable materials for the fabrication of load-bearing prostheses.

One of the variables affecting the longevity of load-bearing implants such as hip-joint implants is the rate of wear of the articulating surfaces and long-term effects of metal ion release. A typical hip-joint prosthesis includes a stem, a femoral head and an acetabular cup against which the femoral head articulates. Wear of either or both of the articulating surfaces results in an increasing level of wear particulates and "play" between the femoral head and the cup against which it articulates. Wear debris can contribute to adverse tissue reaction leading to bone resorption, and ultimately the joint must be replaced.

The rate of wear of the acetabular cup and the femoral head surfaces is dependent upon a number of factors which include the relative hardness and surface finish of the materials which constitute the femoral head and the acetabular cup, the frictional coefficient between the materials of the cup and head, the load applied and the stresses generated at the articulating surfaces. The most common material combinations currently used in the fabrication of hip-joint implants include femoral heads of cobalt or titanium alloys articulating against acetabular cups lined with organic polymers or composites of such polymers including, for instance, ultra-high molecular weight polyethylene (UHMWPE), and femoral heads of polished alumina in combination with acetabular cups lined with an organic polymer or composite or made of polished alumina.

Of the factors which influence the rate of wear of conventional hip-joint implants, the most significant are patient weight and activity level. Additionally, heat which is generated by friction in the normal use of the implant as, for instance, in walking has been shown to cause accelerated creep and wear of the polyethylene cup. Furthermore, there is a correlation between the frictional moment which transfers torque loading to the cup and the frictional coefficient between the femoral head and the surface of the acetabular cup against which the head articulates. Cup torque has been associated with cup loosening. Thus, in general, the higher the coefficient of friction for a given load, the higher the level of torque generated. Ceramic bearing surfaces have been shown to produce significantly lower levels of frictional torque.

It is also noteworthy that two of the three commonly used hip-joint systems as indicated above include a metallic femoral head articulating against a UHMWPE liner inside the acetabular cup. UHMWPE, being a polymeric material, is more susceptible to creep when heated than the commonly used metal alloys or ceramics and is consequently more susceptible to wear than the alloys or ceramics.

It has also been found that metal prostheses are not completely inert in the body. Body fluids act upon the metals causing them to slowly corrode by an ionization process thereby releasing metal ions into the body. Metal ion release from the prosthesis is also related to the articulation and rate of wear of load bearing surfaces because, as may be expected, when a metallic femoral head, for instance, is articulated against UHMWPE, the passive oxide film which forms on the femoral head is constantly removed. The repassivation process constantly releases metal ions during this process. Furthermore, the presence of third-body wear (cement or bone debris) accelerates this process and micro fretted metal particles can increase friction. Consequently, the UHMWPE liner inside the acetabular cup, against which the femoral head articulates, is subjected to accelerated levels of creep, wear, and torque.

U.S. Pat No. 4,145,764 to Suzuki et al recognized that while metal prostheses have excellent mechanical strength they tend to corrode in the body by ionization. Suzuki et al also recognized the affinity between ceramics and bone tissue, but noted that ceramic prostheses are weak on impact resistance. Suzuki et al therefore proposed a metal prosthesis plasma sprayed with a bonding agent which is in turn covered with a porous ceramic coating which would allow the ingrowth of bone spicules into the pores. This combination, it was said, would provide both the mechanical strength of metals and the biocompatibility of ceramics.

The Suzuki patent did not address the issue of friction or wear of orthopedic implant bearing surfaces but confined itself to the single issue of the biocompatibility of metal prostheses. Furthermore, Suzuki et al did not address the issue of dimensional changes that occur when applying a coating or the effect of these dimensional changes in the tightness of fit between the surfaces of an articulating joint prosthesis.

In addition, the application of ceramic coatings to metal substrates often results in non-uniform, poorly-bonded coatings which tend to crack due to the differences in thermal expansion between the ceramic and the underlying metal substrate. Furthermore, such coatings are relatively thick (50-300 microns) and since the bond between the metal and the ceramic coating is often weak there is always the risk of galling or separation of the ceramic coating.

U.S. Pat. No. 3,677,795 to Bokros is directed to the application of a carbide coating over a metallic prosthetic device. This method of forming the carbide coating requires that the prosthesis be heated to temperatures of at least about 1350° C in a reaction chamber through which a hydrocarbon gas such as propane or butane flows. The method is said to produce a prosthetic device which has "excellent compatibility with body tissue and is non-thrombogenic." Bokros does not address the issues of friction, heating, creep and wear of orthopedic implant bearing surfaces, or changes induced in the mechanical properties of the underlying metal due to this high-temperature treatment.

U.S. Pat. No. 3,643,658 to Steinemann is directed to titanium implants coated with titanium oxide, nitride, carbide or carbonitride to prevent corrosion and abrasion of the implant. These coatings are also said to protect the titanium implant from fretting wear. The coatings vary in thickness from 0.08 microns to about 0.15 microns. Despite the teachings of Steinemann, titanium oxide coatings are not as well attached, are not as dense and adherent, and are not effective as protective coatings to prevent metal ion release into the body. Titanium oxide forms naturally on titanium and titanium alloy in ambient conditions. This oxide film is thin (0.5-7 nm) to a point where it is transparent to the naked eye and is similar to the protective passive oxide layers formed primarily from the chromium content in cobalt alloys and stainless steels. Formation of these types of natural passive oxide layers under ambient conditions or nitric acid passivation conditions (usually used for metal orthopaedic implants) can easily abrade off from motion and contact against surrounding material, even soft polymeric materials. Under these conditions, metal ions are released into the environment. For the case of titanium and titanium alloys, amorphous titanium monoxide (TiO) forms at room temperature with small quantities of $Ti_3O_5$. The oxide is easily disturbed in a saline environment resulting in repassivation of an intermediate oxide $3Ti_2O_3 \cdot 4TiO_2$. Formation of the higher oxide, $TiO_2$ (anatase) and $Ti_2O$ occur at higher oxidation temperatures. However, under fretting conditions (with adjacent bone, bearing against polyethylene, and particularly against metal as in the case for bone screws in bone plates, etc.) all forms of normal passivated, and even high-temperature (350° C.) surface anodized titanium oxide films provide little, if any, protection from spalling of the oxide and subsequent fretting of the metal substrate. Relatively thicker coatings using high current-density anodizing also provide little anti-fretting protection due to the poor adherence of the loose powdery films. In general, titanium oxide films are ineffective against fretting conditions because of their poor strength and attachment.

A totally inert, abrasion resistant monolithic ceramic may be ideal for eliminating fretting and metal ion release. For example, zirconium dioxide ($ZrO_2$) and alumina ($Al_2O_3$) have been shown to be highly inert, biocompatible implant materials. These ceramics have been in use recently as monolithic alumina or zirconium dioxide femoral heads in total hip replacements. Both materials are hard, dense, biocompatible, and sufficiently strong. Importantly, when polished, the ceramic bearing surface, articulating against ultra high molecular weight polyethylene (UHMWPE), not only significantly reduces the frictional moment against the UHMWPE cup but also greatly reduces the rate of wear of the UHMWPE. During articulation, no metal ions or micron-size fretted particulates from the ceramic are produced. Thus, these ceramics are advantageous over cobalt, stainless steel, and titanium alloy bearing surfaces. Micron-size metal fretting debris which occurs from metal bearing surfaces is osteolytic (can kill bone cells). However monolithic ceramics are difficult and costly to manufacture, can crack (fragment) under extreme impact, and have a relatively high elastic modulus. Thus, the use of such ceramic materials in monolithic form is not practical in femoral components for total knee prostheses.

Currently-used cobalt alloy knee femoral components have been used successfully for many years. However, measurable levels of potentially toxic metal ions and osteolytic micron fretting debris can be generated. Further, the frictional torque against UHMWPE tibial bearing surfaces and the wear rate of the UHMWPE surface is less than optimal. A ceramic femoral knee prosthesis would be expected to reduce wear and torque due to lower friction and would eliminate metal ion release. However, a monolithic ceramic femoral knee component would be costly, difficult to manufacture because of the complex shape, and would still be highly susceptible to impact fracture due to the thin cross-section. The high modulus ceramic would also limit load transfer to the underlying bone. Such loading is imperative for maintaining viable, supportive bone in non-cemented implants. Additionally, a monolithic ceramic knee femoral component would be difficult to manufacture with a porous coated surface for bone ingrowth. Because limited bone ingrowth is observed with existing porous metal coatings, and because these currently-used metal coatings cannot be effectively or optimally protected by their own oxide, a thin ceramic coating on a porous metal surface would be ideal. To improve load transfer the lower modulus titanium alloys, protected from abrasion using ion-implantation techniques, have been tried as knee femoral components. However, such coatings are extremely thin (about 0.1 micron) and exhibit only an infinitesimal improvement in metal ion release over titanium alloy fretting against UHMWPE. Moreover, ion-implantation does not eliminate production of micron size fretting debris from the surface particularly in the presence of third-body debris, such as bone cement particulates, and does not improve wear of the UHMWPE.

Particulates of metal fretted from metal bearing surfaces can retard growth of bone cells. Polyethylene wear debris produces a severe inflammatory response and a proliferation of giant cells and enzyme response which can lead to loosening and eventual revision of the implant. Thus, the optimum knee or hip joint femoral component is one in which an inert, low friction, low wear (of the UHMWPE) ceramic bearing surface is present, but without the fracture susceptibility and stiffness of monolithic ceramic.

There exists a need for a metal alloy-based orthopedic implant having low friction, highly wear resistant load bearing surfaces which may be implanted for the lifetime of the recipient. There also exists a need for a metal alloy-based orthopedic implant that is not prone to corrosion by the action of body fluids so that it is biocompatible and stable over the lifetime of the recipient.

SUMMARY OF THE INVENTION

The invention provides zirconium or zirconium-containing metal alloy prostheses coated with zirconium nitride or blue-black or black zirconium oxide. The blue-black/black zirconium oxide or nitride coating provides the invention prosthesis with a thin, dense, low friction, wear resistant, biocompatible surface ideally suited for use on articulating surfaces of joint prostheses wherein a surface or surfaces of the joint articulates, translates or rotates against mating joint surfaces. The zirconium oxide or nitride coating may therefore be usefully employed on the femoral heads or inside (metal shell) surfaces of acetabular cups of hip-joint implants or on the articulating surfaces of other types of prostheses, such as femoral and tibial (miniscal bearing) surfaces of knee joints. The blue-black/black zirconium oxide or nitride coatings are also useful for coating multi-component surgical implants subject to microfretting wear. These multi-component implants include, for example, bone plates and screws, compression hip screws and the like.

When a blue-black/black zirconium oxide or nitride-coated joint surface is employed in a manner wherein it articulates or rotates against a non-metallic or non-zirconium oxide or nitride-coated surface, the low friction characteristic of the coating causes reduced friction, wear, and heat generation relative to prior art prostheses. This reduced heat generation results in a lowered tendency for the non-metallic or non-zirconium oxide or nitride coating bearing surface to experience creep and torque so that the useful life of the opposing surface is enhanced. Thus, for instance, where the zirconium oxide or nitride coated femoral head of a hip joint implant articulates against an opposing ultra-high molecular weight polyethylene (UHMWPE) surface liner of an acetabular cup, friction and wear is reduced so that the UHMWPE is subjected to lower levels of torque, wear, and heat generation. Consequently the UHMWPE experiences lowered levels of creep and cup loosening is reduced resulting in an enhancement of the life of the liner and the prosthesis.

Since blue-black/black zirconium oxide and nitride are hard, wear resistant compositions, these coatings are useful in those implants subject to microfretting wear. Thus, for instance, zirconium oxide or nitride coated bone plates and screws have improved fretting resistance.

The zirconium oxide or nitride coating of the subject invention is also useful in providing a biocompatible, inert ceramic barrier between the zirconium-containing metal alloy-based prosthesis and body fluids. Thus, since the zirconium oxide or nitride surface is not prone to ionization and wear-induced corrosion, both the life span and the biocompatibility of the prosthesis are enhanced.

Additionally, the preferred natural in situ formation of a blue-black/black zirconium oxide coating from the presence of zirconium in the substrate metal involves oxygen diffusion into the metal substrate below the oxide coating. Oxygen, an alloying constituent in zirconium, increases the strength of the metal substrate, particularly the fatigue strength. Resistance to fatigue loading is paramount in many orthopedic implant applications such as the hip stem, and femoral and tibial knee components. Thus, not only does the formation of the zirconium oxide coating improve wear, friction, and corrosion resistance, it also improves the mechanical integrity of the implant device from a strength standpoint.

DETAILED DESCRIPTION OF THE PREFERRED EMBODIMENTS

One aspect of the invention is to provide low friction, wear resistant coatings on the articulating surfaces of prosthetic devices. Illustrative examples of such articulating surfaces are shown in the schematic diagrams, FIGS. 1–4.

Figure 1:
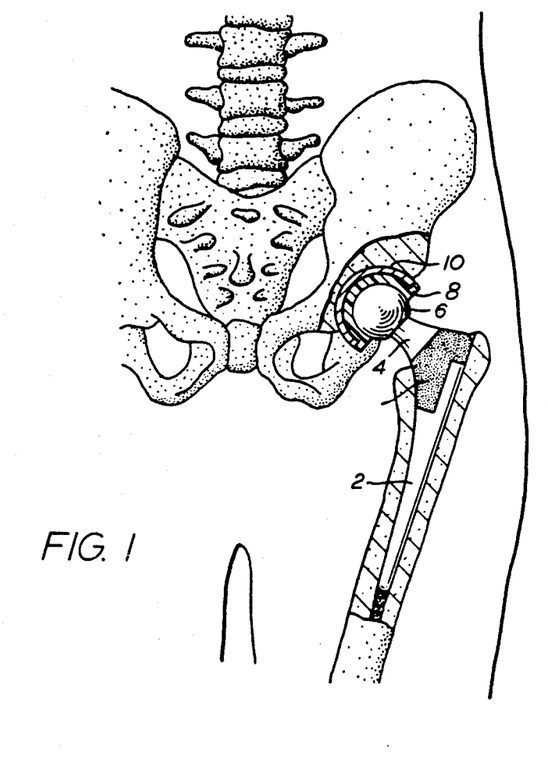
FIG. 1 is a schematic diagram depicting a hip joint prosthesis in position.
Figure 2:
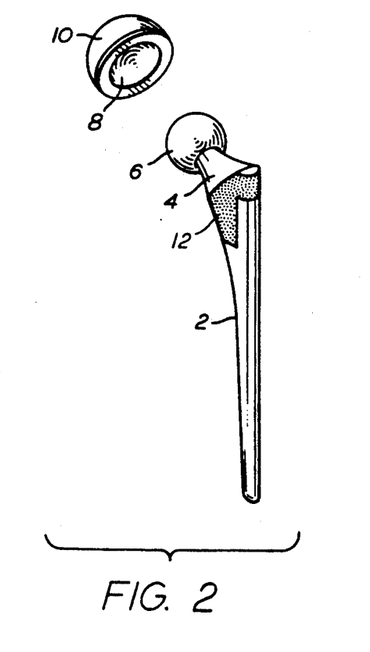
FIG. 2 is a schematic diagram showing a typical hip joint prosthesis.

A typical hip joint assembly is shown in situ in FIG. 1. The hip joint stem 2 fits into the femur while the femoral head 6 of the prosthesis fits into and articulates against the inner lining 8 of an acetabular cup 10 which in turn is affixed to the pelvis as shown in FIG. 1. A porous metal bead or wire mesh coating 12 may be incorporated to allow stabilization of the implant by ingrowth of surrounding tissue into the porous coating. Similarly, such a coating can also be applied to the acetabular component. The femoral head 6 may be an integral part of the hip joint stem 2 or may be a separate component mounted upon a conical taper at the end of the neck 4 of the hip joint prosthesis. This allows the fabrication of a prosthesis having a metallic stem and neck but a femoral head of some other material, such as ceramic. This method of construction is often desirable because ceramics have been found to generate less frictional torque and wear when articulating against the UHMWPE lining of an acetabular cup. Additionally, zirconia ceramic has been shown to produce less wear of the UHMWPE than alumina. Regardless of the materials, however, the femoral head articulates against the inner surface of the acetabular cup thereby causing wear and, in the long term, this may necessitate prosthesis replacement. This is especially the case where the femoral head is of metal and the acetabular cup is lined with an organic polymer or composite thereof. While these polymeric surfaces provide good, relatively low friction surfaces and are biocompatible, they are, as explained above, subject to wear and accelerated creep due to the frictional heat and torque to which they are subjected during ordinary use.

Figure 3:
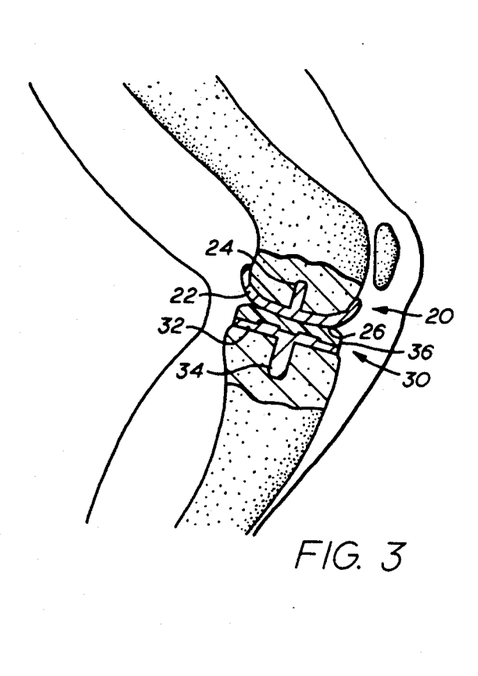
FIG. 3 is a schematic diagram of a knee joint prosthesis in place.
Figure 4:
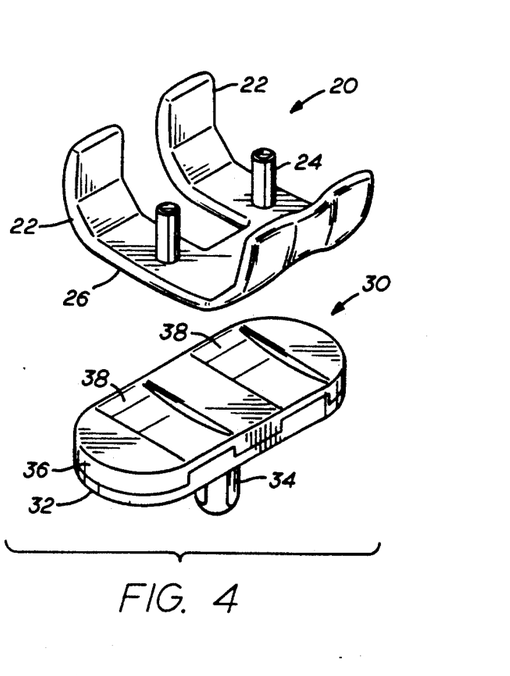
FIG. 4 is a schematic diagram of the parts of a typical knee joint.
Figure 5A:
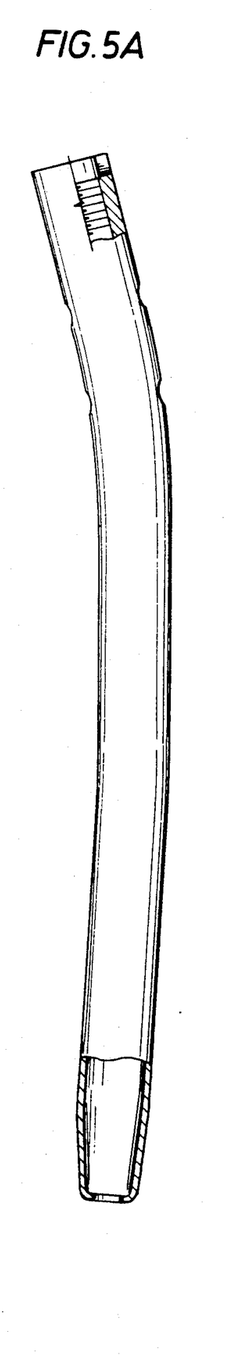
FIG. 5A is a schematic diagram of a side view of a typical intramedullary rod used in orthopedic applications.
Figures 5B, 6A, 6B, 7:
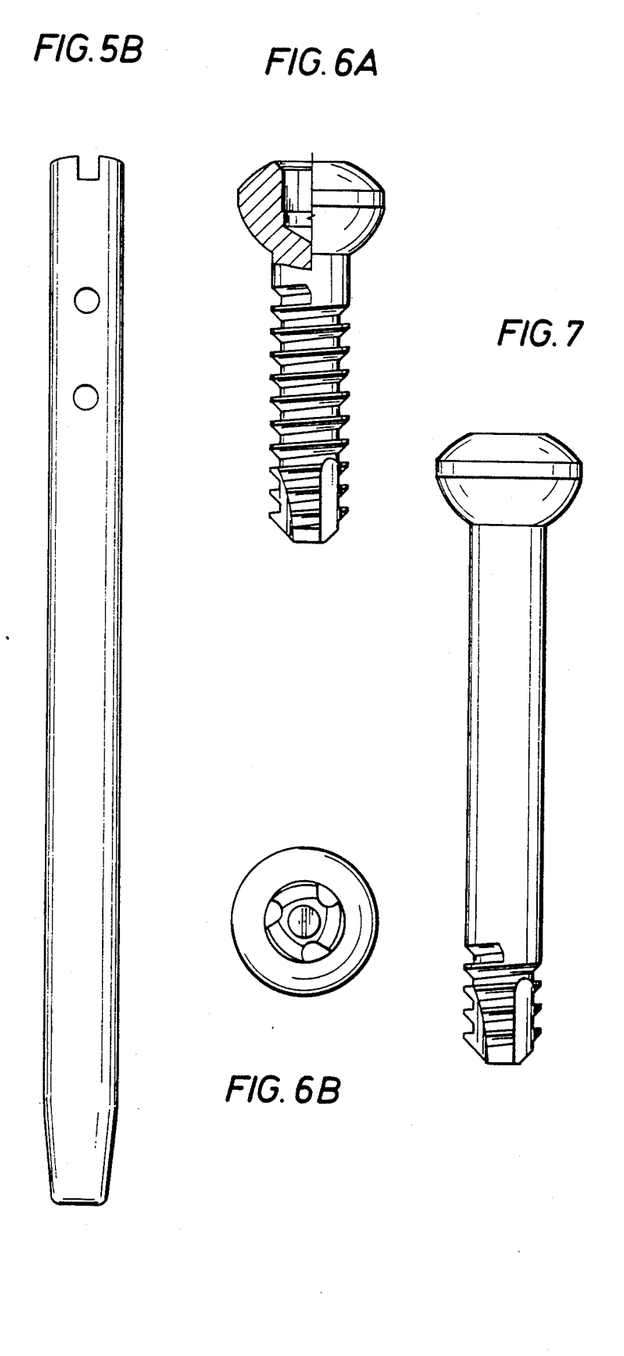
FIG. 5B is a view of 5A, rotated by 90°.
FIG. 6A is a schematic diagram of a typical bone screw.
FIG. 6B is an end view of 6A.
FIG. 7 is a schematic diagram showing a typical screw for affixing bone plates.
Figures 8, 9A, 9C:
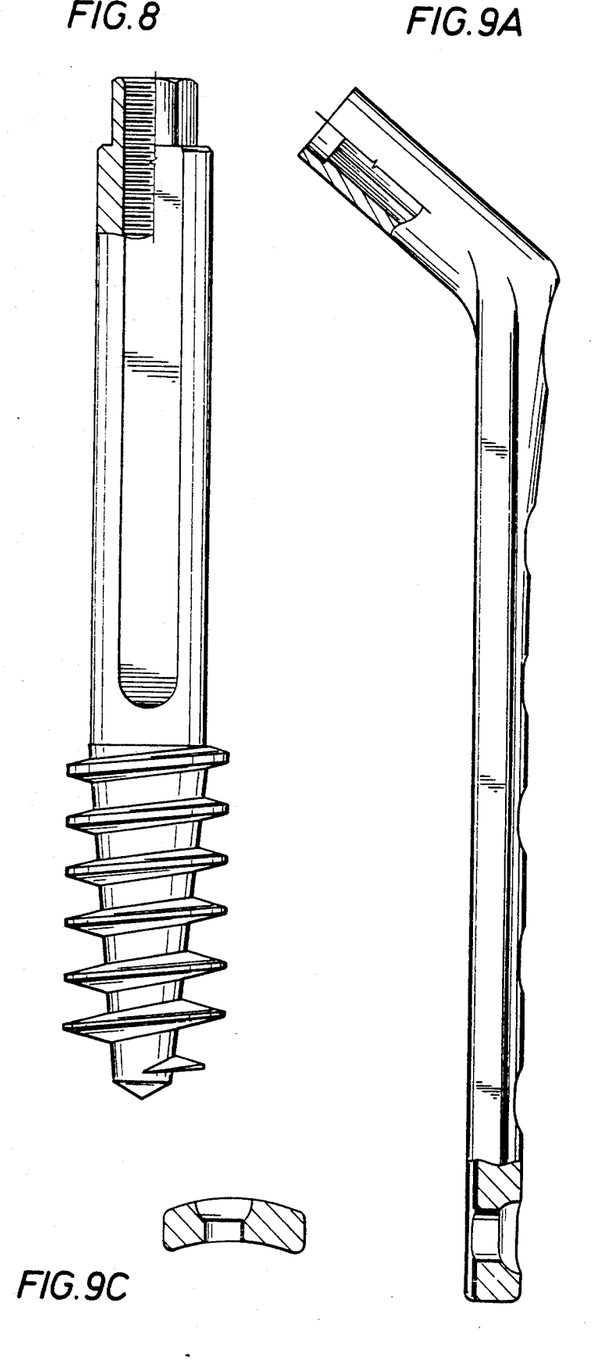
FIG. 8 is a schematic diagram of a compression hip screw.
FIG. 9A is a side view of a typical bone plate, in partial cross-section, for securing to the hip.
FIG. 9C is a cross-sectional view of 9B taken at 9C—9C.
Figure 9B:
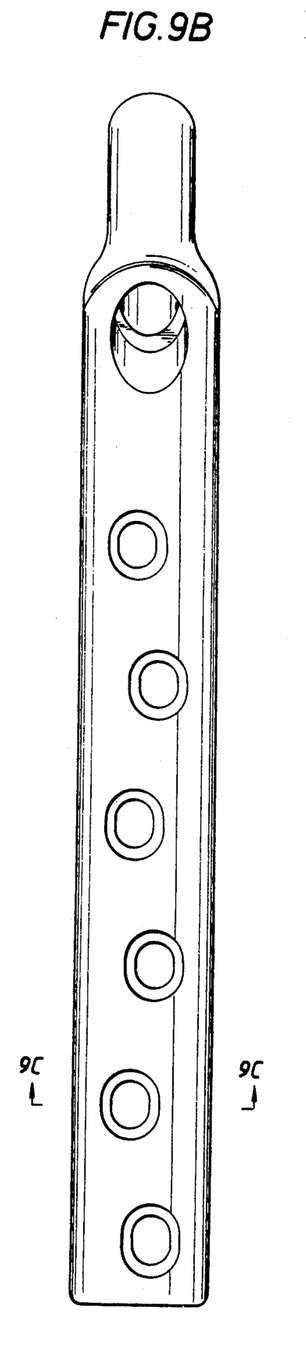
FIG. 9B is the plate of 9A rotated by 90° to show 6 holes for bone screws to affix the plate in the body and a topmost hole fore receiving a compression hip screw, like that of FIG. 8.

A typical knee joint prosthesis is shown in situ in FIG. 3. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. While condyles are typically fabricated of metals, the tibial platform may be made from an organic polymer or a polymer-based composite. Thus, the hard metallic condyle surfaces 26 would articulate against a relatively softer organic composition. As previously explained, this may result in wear of the organic material, i.e. the tibial platform necessitating the replacement of the prosthesis. Miniscal bearing designs of the tibial component can allow for greater contact area without significant sacrifice of knee constraint, thereby reducing wear. Ceramic coatings of both the knee femoral component and the miniscal bearing features in the tibia will further reduce wear of the polyethylene. As in the case of the hip joint, porous bead or wire mesh coatings can also be applied to either the tibial or femoral components of the knee or both.

Multi-component surgical implants such as bone plates and screws, compression hip screws and other implants subject to microfretting wear may be advantageously coated with blue-black or black zirconium oxide or zirconium nitride to provide implants of increased fretting resistance. It is desirable that the bone plates or other implants be machined and drilled before surface oxidation or nitridation to ensure that machined surfaces such as, for instance, drilled hole surfaces, are coated. Thus, when a coated screw is fitted securely into a coated bone plate, the coated surfaces in contact with each other are relatively harder than the uncoated metal would have been. Consequently, microfretting is significantly reduced.

The invention provides blue-black or black zirconium oxide or zirconium nitride coated orthopedic implants or prostheses fabricated of zirconium or zirconium containing metal alloys or a thin coating of zirconium or zirconium alloy on conventional orthopedic implant materials. In order to form continuous and useful zirconium oxide or nitride coatings over the desired surface of the metal alloy prosthesis substrate, the metal alloy should contain from about 80 to about 100 wt. % zirconium, preferably from about 95 to about 100 wt. %. Oxygen, niobium, and titanium include common alloying elements in the alloy with often times the presence of hafnium. Yttrium may also be alloyed with the zirconium to enhance the formation of a tougher, yttria-stabilized zirconium oxide coating during the oxidation of the alloy. While such zirconium containing alloys may be custom formulated by conventional methods known in the art of metallurgy, a number of suitable alloys are commercially available. These commercial alloys include among others Zircadyne 705, Zircadyne 702, and Zircalloy.

The base zirconium containing metal alloys are cast or machined from wrought metal stock by conventional methods to the shape and size desired to obtain a prosthesis substrate. The substrate is then subjected to process conditions which cause the natural (in situ) formation of a tightly adhered, diffusion-bonded coating of zirconium oxide on its surface. The process conditions include, for instance, air, steam, or water oxidation or oxidation in a salt bath. These processes ideally provide a thin, hard, dense, blue-black or black, low-friction wear-resistant zirconium oxide film or coating of thicknesses typically less than several microns ($10^{-6}$ meters) on the surface of the prosthesis substrate. Below this coating, diffused oxygen from the oxidation process increases the hardness and strength of the underlying substrate metal.

Unlike the prior art titanium oxides of, for example, Steinemann's U.S. Pat. No. 3,643,658, the oxygen supplied to form the blue-black or black zirconium oxide coatings of the invention is a beneficial alloying component which improves the fatigue strength of the underlying zirconium metal thereby increasing the potential life of the prosthesis. In contrast, oxygen in titanium alloys tends to stabilize the lower strength α-phase which significantly reduces the metal's fatigue strength.

The air, steam and water oxidation processes are described in now-expired U.S. Pat. No. 2,987,352 to Watson, the teachings of which are incorporated by reference as though fully set forth. The air oxidation process provides a firmly adherent black or blue-black layer of zirconium oxide of highly oriented monoclinic crystalline form. If the oxidation process is continued to excess, the coating will whiten and separate from the metal substrate. The oxidation step may be conducted in either air, steam or hot water. For convenience, the metal prosthesis substrate may be placed in a furnace having an oxygen-containing atmosphere (such as air) and typically heated at 700–1100° F. up to about 6 hours. However, other combinations of temperature and time are possible. When higher temperatures are employed, the oxidation time should be reduced to avoid the formation of the white oxide.

It is preferred that a blue-black zirconium oxide layer ranging in thickness from about 1 to about 5 microns should be formed. For example, furnace air oxidation at 1000° F. for 3 hours will form an oxide coating on Zircadyne 705 about 3-4 microns thick. Longer oxidation times and higher oxidation temperatures will increase this thickness, but may compromise coating integrity. For example, one hour at 1300° F. will form an oxide coating about 14 microns in thickness, while 21 hours at 1000° F. will form an oxide coating thickness of about 9 microns. Of course, because only a thin oxide is necessary on the surface, only very small dimensional changes, typically less than 10 microns over the thickness of the prosthesis, will result. In general, thinner coatings (1–4 microns) have better attachment strength.

The thickness of the blue-black or black zirconium oxide coatings on the invention prostheses provides a further distinction between the invention and the titanium oxide coatings of U.S. Pat. No. 3,643,658 to Steinemann. Titanium oxide films, whether prepared by high temperature (350° C.) oxidation or high current density anodizing, are thin, powdery and loosely adherent. Consequently, these films can be more easily removed under fretting conditions in vivo exposing metal surface to bodily fluids with resulting metal ion release into the body tissue. The thicker, crystalline, more tightly adherent blue-black or black zirconium oxide films, by contrast, do not readily spall or separate from the alloy substrate. It is speculated that the diffusion of oxygen into the zirconium alloy provides a natural interlayer to which the zirconium oxide can adhere readily and tightly. Consequently, these zirconium oxide coatings provide excellent protection against corrosion by bodily fluids.

One of the salt-bath methods that may be used to apply the zirconium oxide coatings to the metal alloy prosthesis, is the method of U.S. Pat. No. 4,671,824 to Haygarth, the teachings of which are incorporated by reference as though fully set forth. The salt-bath method provides a similar, slightly more abrasion resistant blue-black or black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the '824 patent prefers the range 550°-800° C. (1022°-1470° C.). However, the lower oxygen levels in the bath produce thinner coatings than for furnace air oxidation at the same time and temperature. A salt bath treatment at 1290° F. for four hours produces an oxide coating thickness of roughly 7 microns.

Whether air oxidation in a furnace or salt bath oxidation is used, the zirconium oxide coatings are quite similar in hardness. For example, if the surface of a wrought Zircadyne 705 (Zr, 2-3 wt. % Nb) prosthesis substrate is oxidized, the hardness of the surface shows a dramatic increase over the 200 Knoop hardness of the original metal surface. The surface hardness of the blue-black zirconium oxide surface following oxidation by either the salt bath or air oxidation process is approximately 1700-2000 Knoop hardness.

These diffusion-bonded, low friction, highly wear resistant zirconium oxide coatings are applied to the surfaces of orthopedic implants subject to conditions of wear. Such surfaces include the articulating surfaces of knee joints, elbows and hip joints. As mentioned before, in the case of hip joints, the femoral head and stem are typically fabricated of metal alloys while the acetabular cup may be fabricated from ceramics, metals or organic polymer-lined metals or ceramics.

When the zirconium oxide coated femoral head is used in conjunction with any of these acetabular cups, the coefficient of friction between the femoral head and the inner surface of the cup is reduced so that less heat and torque is generated and less wear of the mating bearing surface results. This reduction in heat generation, frictional torque, and wear is particularly important in the case of acetabular cups lined with organic polymers or composites of such polymers. Organic polymers, such as UHMWPE, exhibit rapidly increased rates of creep when subjected to heat with consequent deleterious effect on the life span of the liner. Wear debris of the polymer leads to adverse tissue response and loosening of the device. Thus, not only does the zirconium oxide coating serve to protect the prosthesis substrate to which it is applied and increase its mechanical strength properties but, as a result of its low friction surface, it also protects those surfaces against which it is in operable contact and consequently enhances the performance and life of the prosthesis.

The usefulness of zirconium oxide coated prosthesis is not limited to load bearing prostheses, especially joints, where a high rate of wear may be encountered. Because the zirconium oxide coating is firmly bonded to the zirconium alloy prosthesis substrate, it provides a barrier between the body fluids and the zirconium alloy metal thereby preventing the corrosion of the alloy by the process of ionization and its associated metal ion release.

Oxygen diffusion into the metal substrate during oxidation also increases the strength of the metal. Consequently, a zirconium oxide coated prosthesis may be expected to have a greater useful service life.

Zirconium or zirconium alloy can also be used to provide a porous bead or wire mesh surface to which surrounding bone or other tissue may integrate to stabilize the prosthesis. These porous coatings can be treated simultaneously by the oxidation treatment in a manner similar to the oxidation of the base prosthesis for the elimination or reduction of metal ion release. Furthermore, zirconium or zirconium alloy can also be used as a surface layer applied over conventional implant materials prior to in situ oxidation and formation of the zirconium oxide coating.

In situ oxidation is the preferred method for producing the invention oxide coatings because it allows oxygen diffusion into the metal substrate thereby allowing the formation of a tightly adherent oxide coating while also strengthening the zirconium metal. Other techniques, such as depositing an oxide coating on the prosthesis substrate may also be used but the coatings produced may not be as effective as those produced by the in situ process. Thus, chemical or physical vapor deposition methods may be used, especially those using an ion-assisted deposition method.

While the above discussion has dealt mainly with blue-black or black zirconium oxide coatings on prostheses, zirconium nitride coatings are also effective in reducing wear on opposing surfaces and preventing corrosion of the underlying substrate by bodily fluids.

Even though air contains about four times as much nitrogen as oxygen, when zirconium or a zirconium alloy is heated in air as described above, the oxide coating is formed in preference to the nitride coating. This is because the thermodynamic equilibrium favors oxidation over nitridation under these conditions. Thus, to form a nitride coating the equilibrium must be forced into favoring the nitride reaction. This is readily achieved by elimination of oxygen and using a nitrogen or ammonia atmosphere instead of air or oxygen when a gaseous environment (analogous to "air oxidation") is used.

In order to form a zirconium nitride coating of about 5 microns in thickness, the zirconium or zirconium alloy prosthesis should be heated to about 800° C. for about one hour in a nitrogen atmosphere. Thus, apart from the removal of oxygen (or the reduction in oxygen partial pressure), or increasing the temperature, conditions for forming the zirconium nitride coating do not differ significantly from those needed to form the blue-black or black zirconium oxide coating. Any needed adjustment would be readily apparent to one of ordinary skill in the art.

When a salt bath method is used to produce a nitride coating, then the oxygen-donor salts should be replaced with nitrogen-donor salts, such as, for instance cyanide salts. Upon such substitution, a nitride coating may be obtained under similar conditions to those needed for obtaining an oxide coating. Such modifications as are necessary, may be readily determined by those of ordinary skill in the art.

Alternatively, the zirconium nitride may be deposited onto the zirconium or zirconium alloy surface via standard physical or chemical vapor deposition methods, including those using an ion-assisted deposition method. It is preferred that the physical or chemical vapor deposition methods be carried out in an oxygen-free environment. Techniques for producing such an environment are known in the art, for instance the bulk of the oxygen may be removed by evacuation of the chamber and the residual oxygen may be removed with an oxygen getter.

When the zirconium or zirconium alloy is provided with a zirconium porous bead or zirconium wire mesh surface, then this surface layer can also be coated with zirconium nitride to provide protection against metal ionization in the body.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

I claim:

1. A prosthesis for implantation in a patient, comprising:

(a) a prosthesis body selected from the group consisting of bone plates, screws and compression hip screws, said prosthesis body being formed of zirconium or zirconium alloy, at least a portion of said prosthesis body being adapted to penetrate and engage body tissue; and (b) a coating of thickness from about 1 to about 5 microns selected from the group consisting of blue-black zirconium oxide, black zirconium oxide and zirconium nitride, said coating formed in situ on at least the portion of the prosthesis body adapted to penetrate and engage body tissue for reducing microfretting of the coated prosthesis portion engaging and penetrating the body tissue.

2. The prosthesis of claim 1, wherein the prosthesis body further comprises an irregular surface structure adapted to accommodate tissue ingrowth on the portion of the prosthesis body adapted to penetrate and engage body tissue.

3. The prosthesis of claim 2, wherein the irregular surface structure is formed of zirconium or zirconium alloy beads connected to the outer surface of the prosthesis body.

4. The prosthesis of claim 2, wherein the irregular surface structure is formed of a zirconium or zirconium alloy wire mesh connected to the outer surface of the prosthesis body.

5. The prosthesis of claim 1, wherein the entire prosthesis body is covered with the thin coating of zirconium oxide or zirconium nitride.

* * * * *